United States Patent
Greenwood et al.

(10) Patent No.: US 7,002,025 B2
(45) Date of Patent: Feb. 21, 2006

(54) PROCESS FOR THE PREPARATION OF CITALOPRAM

(75) Inventors: Alan K. Greenwood, London (GB); Derek McHattie, Stotfold (GB); Josef A. Rechka, Slip End (GB); Paul C. M. Hedger, Arlesey (GB); Mark P. Gamble, Hitchin (GB)

(73) Assignee: Resolution Chemicals Limited (GB)

(*) Notice: Subject to any disclaimer, the term of this patent is extended or adjusted under 35 U.S.C. 154(b) by 282 days.

(21) Appl. No.: 10/221,012

(22) PCT Filed: Mar. 7, 2001

(86) PCT No.: PCT/GB01/00994

§ 371 (c)(1), (2), (4) Date: Dec. 16, 2002

(87) PCT Pub. No.: WO01/66536

PCT Pub. Date: Sep. 13, 2001

(65) Prior Publication Data

US 2004/0014997 A1 Jan. 22, 2004

(30) Foreign Application Priority Data

Mar. 7, 2000 (GB) ............................ 0005477

(51) Int. Cl.
C07D 307/78 (2006.01)

(52) U.S. Cl. .................... 549/467; 549/469

(58) Field of Classification Search ............ 549/467, 549/469
See application file for complete search history.

(56) References Cited

U.S. PATENT DOCUMENTS

| 3,607,884 A | 9/1971 | Forney |
| 5,691,362 A | 11/1997 | McCormick et al. |
| 5,817,677 A | 10/1998 | Linz et al. |
| 6,204,284 B1 | 3/2001 | Beer et al. |

FOREIGN PATENT DOCUMENTS

| DE | 2 242 007 | 3/1974 |
| DE | 195 39 091 A1 | 4/1997 |
| DE | 199 83 486 C2 | 9/2002 |
| EP | 0 461 079 B1 | 12/1991 |
| EP | 0 347 066 B1 | 3/1995 |
| EP | 1 095 926 A2 | 5/2001 |
| EP | 1 125 907 A2 | 8/2001 |
| EP | 1 118 614 B1 | 6/2002 |
| GB | 1 526 331 | 9/1978 |
| GB | 1 578 989 | 11/1980 |
| WO | WO 95/15941 | 6/1995 |
| WO | WO 98/19511 | 5/1998 |
| WO | WO 98/19512 | 5/1998 |
| WO | WO 98/19513 | 5/1998 |
| WO | WO 99/30548 | 6/1999 |
| WO | WO 00/23431 | 4/2000 |
| WO | WO 00/35859 | 6/2000 |
| WO | WO 01/02383 A2 | 1/2001 |
| WO | WO 01/03694 A1 | 1/2001 |
| WO | WO 01/22941 A1 | 4/2001 |
| WO | WO 01/32642 A1 | 5/2001 |
| WO | WO 01/32643 A1 | 5/2001 |
| WO | WO 01/41701 A2 | 6/2001 |
| WO | WO 01/43740 A1 | 6/2001 |
| WO | WO 01/47909 A1 | 7/2001 |
| WO | WO 01/49672 A1 | 7/2001 |
| WO | WO 01/51477 A1 | 7/2001 |
| WO | WO 01/51478 A1 | 7/2001 |
| WO | WO 01/62754 A1 | 8/2001 |

OTHER PUBLICATIONS

Dordor, et al., *Reaction of Oxoazolines with Phosphorus Oxychloride*, Tetrahedron Letters, 1983, vol. 24, No. 13, pp. 1437–1440.

Meyers, et al., *Nucleophilic Aromatic Substitution on o-(Methoxy)aryloxazolines. A Convenient Synthesis of o-Alkyl-, o-Alkylidene-, and o-Arylbenzoic Acids*, J. Org. Chem., 1978, vol. 43, No. 7, pp. 1372–1379.

*Primary Examiner*—Amelia A. Owens
(74) *Attorney, Agent, or Firm*—Hodgson Russ LLP

(57) ABSTRACT

Preparation of citalopram comprises the steps of: (a) converting the compound of Formula (I) to a compound of Formula (II), wherein R in Formula (I) represents a $C_2$ to $C_5$ alkylene group which may be substituted or unsubstituted, and $R^1$ in the compounds of Formula (II) represents a carboxylic acid group or a salt or an ester thereof; and (b) converting the compound of Formula (II) to form citalopram or a pharmaceutically acceptable salt thereof, or a direct conversion of the compound of Formula (I) to citalopram

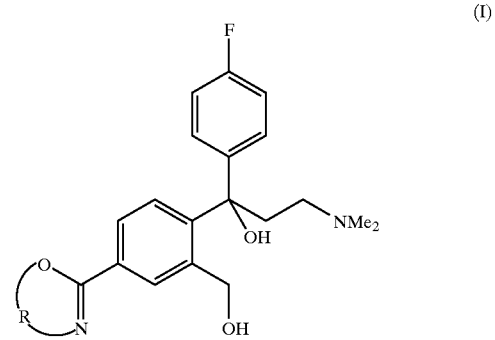

(I)

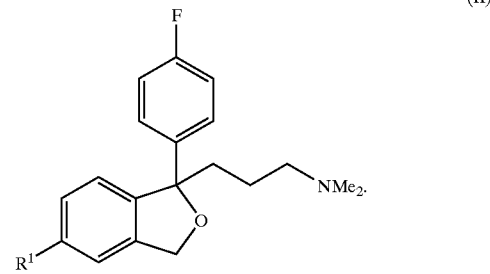

(II)

35 Claims, No Drawings

PROCESS FOR THE PREPARATION OF CITALOPRAM

The present invention relates to a method for the synthesis of the anti-depressant drug citalopram, 1-[3-dimethylamino)propyl}-1-(4-fluoro-phenyl)-1,3-dihydro-isobenzofurancarbonitrile.

Citalopram, which belongs to a class of antidepressant drugs known as selective serotonin reuptake inhibitors, has the following chemical structure:

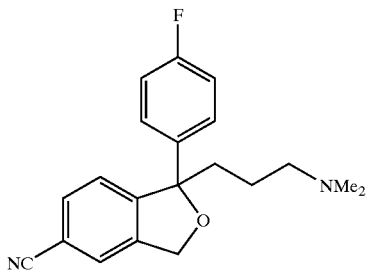

The compound bears a para-fluoro-substituted aromatic ring and an N,N-dimethylaminopropyl substituent at the 1-position. The aromatic moiety of the phthalane ring bears a nitrile group at the 5-position. The major part of the antidepressant activity of citalopram resides in the (+)-enantiomer. Citalopram has also been shown to have potential use in the treatment of obesity and alcoholism (EP 0 347 066).

Citalopram was first disclosed in DE 2,657,271 (U.S. Pat. No. 4,136,193). This patent discloses a synthetic route to form citalopram starting with the 5-bromophthalide:

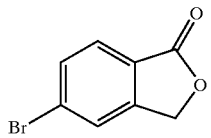

Addition of two successive Grignard reagents, formed from 1,4-bromo-fluorobenzene and N,N-dimethylaminopropyl chloride, to the carbonyl carbon of 5-bromophthalide forms a diol intermediate which is subjected to an acid-catalysed dehydration cyclisation reaction using 60% phosphoric acid, to form the phthalane ring. In order to convert the 5-bromo group of this intermediate into the 5-cyano substituent of citalopram, the compound is subjected to a selective displacement of the 5-bromo group using copper (I) cyanide. This final step involves refluxing the compound with CuCN in dimethylformamide for 4 hours.

U.S. Pat. No. 4,136,193 discloses a process wherein 5-bromophthalide is reacted with a Grignard reagent formed from 1,4-bromofluorobenzene and the resulting carbonyl compound is reduced using LiAlH$_4$ to form a diol intermediate which is subsequently cyclised. The phthalane intermediate is reacted with CuCN to form the 5-cyano group. Addition of the N,N-dimethylaminopropyl side chain is effected by deprotonation of the carbon a to the fluorophenyl group, with the resulting anion being quenched with N,N-dimethylaminopropyl chloride to form citalopram.

U.S. Pat. No. 3,467,675 discloses an alternative method of cyclising the 5-bromo diol intermediate referred to in U.S. Pat. No. 4,136,193, wherein the diol is reacted with a mixture of glacial acetic acid and concentrated hydrochloric acid to form a phthalane intermediate.

EP-A-0 347 066 discloses a procedure for cyclising a diol intermediate to form the phthalane ring of citalopram using a mesylate ester. The same publication also discloses activation of the primary hydroxyl group by generation of a chiral ester to enable the separate diastereomers to be separated, to produce enantiomerically pure citalopram.

In the prior art processes outlined above, the para-fluorophenyl- and N,N-dimethylaminopropyl substituents of citalopram are formed either by the addition of two successive Grignard reagents, or the addition of a Grignard reagent formed from 1,4-bromofluorobenzene and a subsequent deprotonation-alkylation using N,N-dimethylaminopropyl chloride. Thus, these synthetic procedures require the use of at least one Grignard reagent. A problem with the use of Grignard reagents is that there is a risk of side reactions leading to contamination of the product.

It will also be noted that, in the synthetic routes to citalopram described in DE 2,657,271 and U.S. Pat. No. 4,136,193, the 5-nitrile group on the phthalane benzene ring is introduced by an exchange reaction of the 5-bromo analogue using copper (I) cyanide in refluxing dimethylformamide. This has the disadvantage of the high toxicity of the copper cyanide reagent.

An alternative method is to start with a compound in which the eventual 5-position of the phthalane ring contains a substituent that can be converted to a nitrile function. Such procedures are disclosed in International publication nos. WO 98/19511, WO 98/19512 and WO 98/19513. These publications disclose processes involving the use of intermediates containing various substituents in the eventual 5-position of the phthalane ring, such as alkoxycarbonyl or alkylaminocarbonyl. However, the use of an amino or an aminoalkylcarbonyl substituent in WO 98/19512 does not avoid the use of a metal cyanide reagent, because the conversion of these groups to a nitrile substituent involves an initial diazotation reaction and subsequent reaction of the diazo salt with, e.g. CuCN and/or NaCN.

WO 99/30548 discloses a procedure using a 5-substituted phthalane containing the dimethylaminopropyl- and para-fluorophenyl side chains of citalopram, wherein the 5-substituent can be a substituted amide or an optionally substituted 4,5-dihydro-1,3-oxazol-2-yl group. According to the disclosure, the cyano group of citalopram can be formed in a multi-step procedure comprising subjecting the 5-substituted intermediate compound to a reductive hydrolysis reaction using reducing agents such as DIBAL-H, superhydride, LiAlH$_4$ to form the 5-formyl derivative. The 5-formyl derivative is converted to citalopram via formation of e.g. an intermediate oxime. This publication indicates that where the 5-substituent is a 4,5-dihydro-1,3-oxazol-2-yl group, the reductive hydrolysis reaction requires the oxazoline nitrogen atom to be alkylated. This has the disadvantage of introducing a further step in the synthesis route. Although no examples are shown for the alkylation step, the suggested alkylation procedure is via a reaction with methyl iodide or a dialkylsulfate. From the chemistry of the reagents, it is likely that such a process would result in quaternisation of the nitrogen of the amino group in the dimethylaminopropyl side chain. This could substantially decrease yields, and result in an unusable side product, thus wasting valuable starting materials.

In view of the prior art procedures and the problems associated therewith, it is an object of the present invention to provide an alternative process for the synthesis of citalopram or a salt thereof. Further objects of at least specific embodiments of the invention are to eliminate the use of toxic cyanating agents such as CuCN, to provide a process for the synthesis of citalopram that avoids the use of starting materials having functional groups that are unstable to Grignard reagents, to provide a process for the synthesis of citalopram that can be carried out using simple chemical reagents and is therefore economical, and/or to provide a simplified procedure for the synthesis of citalopram that avoids complex, multi-step reactions.

According to one aspect of the invention, there is provided a process for the synthesis of citalopram comprising:
(a) converting a compound of Formula (I):

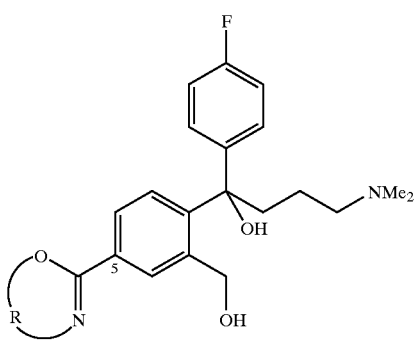
(I)

wherein R represents a $C_2$ to $C_5$ alkylene group which may be unsubstituted or substituted by one or more of the groups selected from: $C_1$ to $C_8$ alkyl (which may be unsubstituted or substituted by halo, $C_1$ to $C_8$ alkoxy, or $C_8$ to $C_{15}$ aryl), $C_3$ to $C_{10}$ cycloalkyl (which may be unsubstituted or substituted by halo, $C_1$ to $C_8$ alkyl, $C_1$ to $C_8$ alkoxy, or $C_8$ to $C_{15}$ aryl), $C_5$ to $C_{10}$ heterocycloalkyl, $C_5$–$C_{15}$ aryl (which may be unsubstituted or substituted by halo, $C_1$ to $C_8$ alkoxy, or $C_1$ to $C_8$ alkyl), $C_7$ to $C_{10}$ aralkyl, $C_1$ to $C_8$ alkoxy and heteroaryl; or the alkylene group can be substituted by one or more $C_3$ to $C_7$ cycloalkyl groups attached to the alkylene group via a spiro-carbon atom, or the alkylene group may contain a $C_8$–$C_{15}$ aryl group fused to two alkylene carbon atoms,
to a compound of Formula (II):

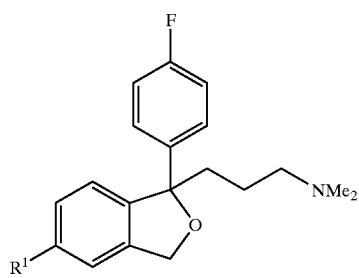
(II)

wherein $R^1$ represents a carboxylic acid group or a salt or an ester thereof; and
(b) converting the compound of Formula (II) to form citalopram or a pharmaceutically acceptable salt thereof.

The R group of the compound of Formula (I) as defined above, is selected such that the substituent in the C-5 position of the eventual phthalane ring (hereinafter designated the "C-5 substituent") can be hydrolysed in a one pot reaction to form the $R^1$ group of the compound of Formula (II).

It should be appreciated that the identity of the R group is not an essential feature of the invention, because the C-5 substituent containing the R group is eventually removed by hydrolysis, or is converted to the cyano group of citalopram in subsequent reaction steps. Thus, the group R is chosen in order to enable the C-5 substituent to be hydrolysed in a one pot reaction to form the $R^1$ group of the compound of Formula (II), or the group R is chosen to enable direct conversion of the C-5 substituent to a cyano group to form citalopram.

Preferably, the group R, taken together with the nitrogen and oxygen atoms forms a five- or six-membered substituted or unsubstituted ring in the C-5 position of the compound of Formula (I). Particularly preferred groups for R include $C_2$ or $C_3$ alkylene, which may be unsubstituted or substituted by one or more groups selected from $C_1$ to $C_6$ alkyl, $C_5$ to $C_{10}$ cycloalkyl, $C_6$ to $C_{15}$ aryl and $C_1$ to $C_6$ alkoxy. Such R groups have the advantage that the C-5 substituent is stable to the Grignard reagents employed in subsequent reaction steps, and therefore minimises or avoids the possibility of side reactions that decrease the yield and purity of the intermediates and final product.

A further preferred R group is such that the C-5 substituent of the compound of Formula (I) is a substituted or unsubstituted five member d ring, i.e. an oxazoline.

In an especially preferred embodiment of the present Invention, the compound of Formula (I) represents

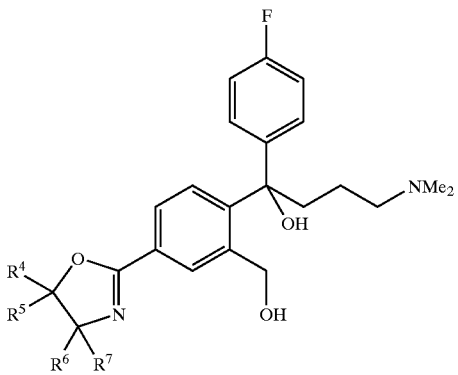

wherein $R^4$, $R^5$, $R^6$ and $R^7$ each independently represents H, $C_1$ to $C_6$ alkyl (which may be unsubstituted or substituted by halo, $C_1$ to $C_6$ alkoxy, or $C_8$ to $C_{15}$ aryl), $C_6$ to $C_{10}$ cycloalkyl (which may be unsubstituted or substituted by halo, $C_1$ to $C_6$ alkyl, $C_1$ to $C_8$ alkoxy, or $C_8$ to $C_{16}$ aryl), $C_1$ to $C_6$ alkoxy, or one of $R^4$ or $R^5$ taken together with one of the $R^6$ or $R^7$ groups form a benzene ring fused to the ethylene carbon atoms of the oxazoline ring, or one or both of the $R^4$ and $R^5$ or $R^6$ and $R^7$ groups taken together represents a $C_3$–$C_8$ cycloalkyl group attached to one or both of the oxazoline ethylene carbon atoms via a spiro carbon.

Preferably $R^6$ and $R^7$ each independently represent H or $C_1$ to $C_6$ alkyl. In a particularly preferred embodiment, $R^4$ and $R^5$ both represent H and $R^6$ and $R^7$ both represent methyl.

In accordance with a preferred embodiment of the present invention, the compound of Formula (II) may be formed by subjecting the compound of Formula (I) to a one-pot reaction, wherein the diol function is ring-closed to form the phthalane and the oxazoline substituent is hydrolysed.

A preferred method of carrying out the conversion of the compound of Formula (I) to form the compound of Formula (II) includes subjecting the compound of Formula (I) to acid hydrolysis followed by base hydrolysis. The reaction may be carried out in one pot, or the reaction may be carried out in two stages, i.e. the reaction is stopped after the acid hydrolysis stage and subjected to a separate base hydrolysis reaction. Advantageously, the acid and base hydrolysis reactions are carried out in a one-pot procedure. Any suitable acid and base may be used in this step. Particularly suitable acids include mineral acids, such as hydrochloric acid, hydrobromic acid, sulfuric acid and phosphoric acid. Hydrochloric acid or sulfuric acid are preferred, with sulfuric acid being an especially preferred reagent. Suitable bases for carrying out the base hydrolysis include sodium hydroxide, potassium hydroxide and lithium hydroxide.

Thus, in a typical one-pot procedure, the compound of Formula (I) is subjected to acid hydrolysis using aqueous sulfuric acid at reflux. The reaction mixture is basified using a suitable base, such as sodium hydroxide either in aqueous solution or as a solid, to form the acid phthalane intermediate of Formula (II) as a sodium salt.

In an alternative procedure according to the process of the present invention, the hydrolysis may be carried out in two stages using hydrochloric acid in the first stage. In this procedure an amino ester intermediate is formed. Thus, for example, where the R group represents an ethylene moiety substituted with $R^4$, $R^5$, $R^6$ and $R^7$ groups, the following amino ester intermediate is formed:

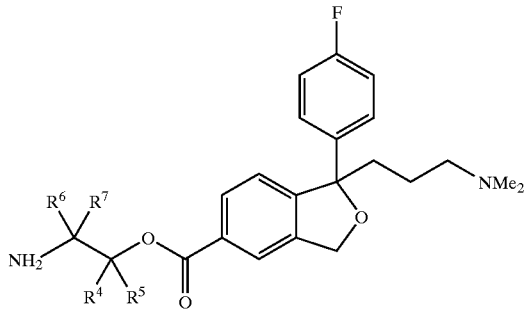

wherein $R^4$, $R^5$, $R^6$ and $R^7$ are as defined as above for Formula (I). Cleavage of the amino ester via a base hydrolysis reaction can be achieved using any suitable base, such as sodium hydroxide, potassium hydroxide and lithium hydroxide, resulting in the formation of the acid of Formula (II). This reaction may be carried out with or without isolation of the amino ester. Preferably the reaction is carried out in one-pot without isolation of the amino ester intermediate.

Alternatively, the acid solvolysis of the compound of Formula (I) may be carried out using a mineral acid in the presence of an alcohol solvent, which is typically a $C_1$ to $C_6$ alcohol such as methanol and ethanol, to form the corresponding ester of Formula (II).

In accordance with a further aspect of the present invention, the compound of Formula (II) is converted to citalopram via an amide intermediate of Formula (III):

(III)

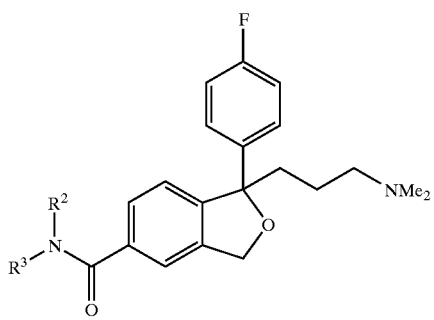

wherein $R^2$ and $R^3$ independently represent H or $C_1$ to $C_6$ alkyl, $C_5$ to $C_{10}$ cycloalkyl, aralkyl or aryl. Preferably each $R^2$ and $R^3$ independently represents H or $^t$Bu. Even more preferably, both $R^2$ and $R^3$ represent H, or one of $R^2$ or $R^3$ represents H, and the other represents $^t$Bu.

The conversion of the compound of Formula (II) to the amide of Formula (III) can be carried out by procedures known in the art. These include the use of thionyl chloride followed by reaction with ammonia, the use of coupling agents such as active esters (e.g. thioesters, nitrophenyl esters), the use of mixed anhydrides, carbodiimides (including DCCI and EDAC), and enzymes. For example, the acid group of the compound of Formula (II) can be converted to an ester and the resulting ester subjected to an aminolysis reaction.

Alternatively, if the hydrolysis of the compound of Formula (I) is carried out using a mineral acid in the presence of an alcohol solvent as described above, the resulting ester derivative can be subjected to an aminolysis reaction to form the amide. Other methods of converting a carboxylic acid group to an amide group will be apparent to the skilled person.

However, in accordance with a preferred embodiment of the invention, the compound of Formula (II) is converted to the amide of Formula (III) via a two step procedure comprising:

(i) converting the compound of Formula (II) wherein $R^3$ represents a carboxylic acid or a salt thereof, to an acid chloride, —COCl; and (ii) converting the acid chloride to the group —C(O)NR$^2$R$^3$, wherein $R^2$ and $R^3$ are as defined as for Formula (III), and preferably, $R^2$ and $R^3$ independently represent H or $^t$Bu, and even more preferably, both $R^2$ and $R^3$ represent H, or one of $R^2$ or $R^3$ represents H, and the other represents $^t$Bu.

The conversion of the compound of Formula (II) to an acid chloride is preferably carried out by reaction with a suitable chlorinating agent. Such suitable chlorinating agents include thionyl chloride, POCl$_3$ and PCl$_5$, PCl$_3$, oxalyl chloride, or a mixture of carbon tetrachloride-triphenylphosphine. A particularly preferred reagent for this conversion is thionyl chloride. In the case of liquid chlorinating agents, the reaction may be carried out in the neat liquid. Alternatively the reaction can be carried out in the presence of a solvent. Suitable solvents for use in this reaction include dichloromethane, dimethylformamide, chloroform, carbon tetrachloride, dimethylacetamide, tetrahydrofuran or toluene.

The acid chloride formed from the above reaction may be converted to the amide of Formula (III) by reaction with ammonia or an amine HNR$^2$R$^3$. Preferably, both $R^2$ and $R^3$ represent H, or one of $R^2$ or $R^3$ represents H, and the other represents $^t$Bu.

The reaction can be carried out in two stages with isolation of the acid chloride, however, for convenience the reaction is preferably carried out in a one-pot procedure. In a typical one-pot procedure, the compound of Formula (II) is reacted with thionyl chloride in dichloromethane solvent. The mixture containing the acid chloride is then subjected to reaction with the appropriate amine or ammonia to form the amide.

The conversion of the amide group in the compounds of Formula (III) to form the corresponding cyano group in citalopram may be carried out by methods known in the art. For example, where the groups $R^2$ and $R^3$ in the compounds of Formula (III) both represent hydrogen, the amide group can be dehydrated using dehydrating agents, such as SOCl$_2$, P$_2$O$_5$, POCl$_3$, PCl$_5$, CCl$_4$—PPh$_3$, TiCl$_4$-base, HMPA and Cl$_3$COCl—Et$_3$N. Compounds of Formula (III) wherein $R^2$ or $R^3$ are other than hydrogen may be converted to the citalopram by reaction with PCl$_5$.

Thus, in a preferred embodiment of the present invention, there is provided a process for the preparation of citalopram comprising the steps of:

(a) subjecting the compound of Formula (I) having the structure:

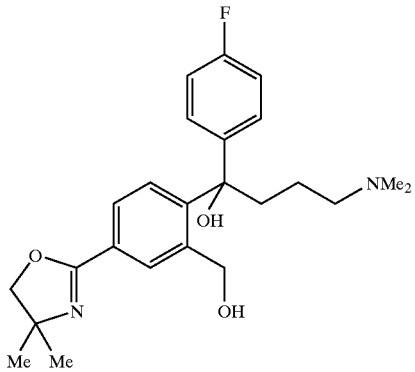

to a ring-closure reaction with aqueous sulfuric acid followed by a hydrolysis reaction with aqueous sodium hydroxide to produce a compound of formula (II) having the structure:

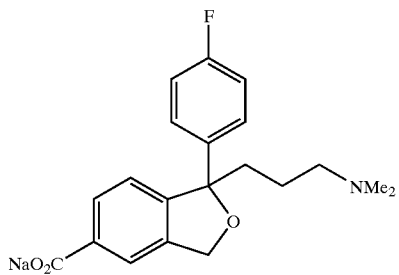

(b) subjecting the compound of Formula (II) to reaction with thionyl chloride followed by reaction with ammonia to form the compound of Formula (III) having the structure:

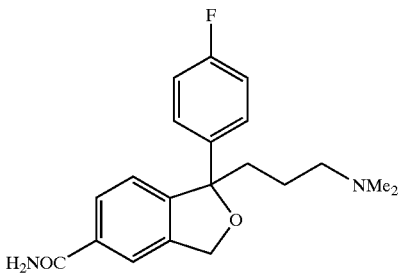

(c) subjecting the compound of Formula (III) to a reaction with POCl₃ to form citalopram.

Preferably, step (b) is carried out as a one-pot process.

The invention further provides the use of a compound of Formula (II), wherein $R^1$ represents a carboxylic add or a salt thereof, in a process for the synthesis of citalopram.

The invention further provides a novel compound having the Formula (II):

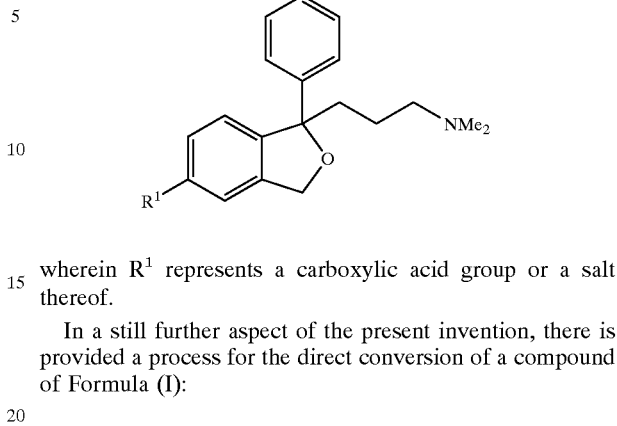

wherein $R^1$ represents a carboxylic acid group or a salt thereof.

In a still further aspect of the present invention, there is provided a process for the direct conversion of a compound of Formula (I):

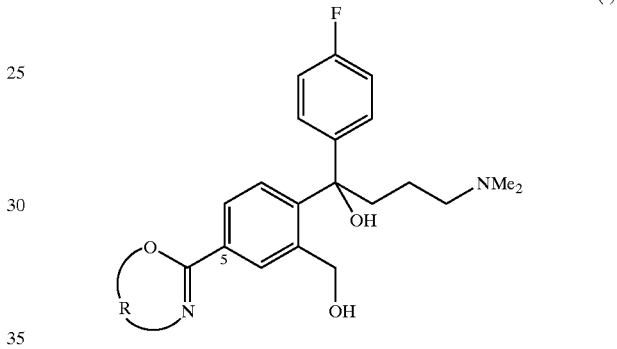

wherein R represents a $C_2$ to $C_5$ alkylene group which may be unsubstituted or substituted by one or more of the groups selected from: $C_1$ to $C_8$ alkyl (which may be unsubstituted or substituted by halo, $C_1$ to $C_6$ alkoxy, or $C_6$ to $C_{15}$ aryl), $C_3$ to $C_{10}$ cycloalkyl (which may be unsubstituted or substituted by halo, $C_1$ to $C_6$ alkyl, $C_1$ to $C_6$ alkoxy, or $C_6$ to $C_{15}$ aryl), $C_5$ to $C_{10}$ heterocycloalkyl, $C_6$–$C_{15}$ aryl (which may be unsubstituted or substituted by halo, $C_1$ to $C_6$ alkoxy, or $C_1$ to $C_6$ alkyl), $C_7$ to $C_{10}$ aralkyl, $C_1$ to $C_6$ alkoxy and heteroaryl; or the alkylene group can be substituted by one or more $C_3$ to $C_7$ cycloalkyl groups attached to the alkylene group via a spiro-carbon atom, or the alkylene group may contain a $C_6$–$C_{15}$ aryl group fused to two alkylene carbon atoms, to citalopram, comprising subjecting the compound of Formula (I) to a one-pot reaction with acidic dehydrating agent.

The acidic dehydrating agent preferably comprises a halide or an oxyhalide is compound of at least one Group V or Group VI element, or a mixture thereof. Thus, for example, the acidic dehydrating agent may have the formula:

$M(N)_m(O)_n(X)_p$ wherein M and N represent a Group V or Group VI atom, X represents a halogen atom and m, n each independently represent 0–2 and p represents 1–5.

Preferred acidic dehydrating agents for this reaction comprise a halide or an oxyhalide compound of phosphorus or sulfur.

Thus, in accordance with a preferred embodiment of the process, the compound of Formula (I), where R is as defined hereinabove, is subjected to reactions with $PCl_3$, $PCl_5$, $POCl_3$ and $SOCl_2$ or a combination of at least two reagents selected from $PCl_3$, $PCl_5$, $POCl_3$ and $SOCl_2$.

In a particularly preferred process, the compound of Formula (I) is converted to citalopram by subjecting the compound of Formula (I), wherein R is as defined as above, to reaction with $PCl_5$, phosphorus oxychloride or a combination of thionyl chloride and phosphorus oxychloride.

In the latter case, where a combination of thionyl chloride and phosphorus oxychloride is used, the reaction is preferably carried out in one pot using $SOCl_2$ followed by $POCl_3$.

Advantageously, this reaction leads to a direct, one-pot conversion of the compound of Formula (I) to citalopram.

The mechanism of the direct conversion of the C-5 substituent of the compound of Formula (I) to form the nitrile group of citalopram is not fully understood. Without wishing to be bound by any particular theory, a possible mechanism is that the reaction proceeds via chlorination to form a chloroimine, followed by fragmentation to the form the nitrile compound.

The reaction is preferably carried out in the presence of a suitable base and/or a basic solvent. Suitable bases for this reaction include organic bases, examples of which include dimethylaminopyridine (DMAP), pyridine, trialkylamines such as triethylamine and Hünig's base ($^iPr_2NEt$), morpholine, N-methylmorpholine and quinoline. A preferred base for this reaction comprises pyridine. Suitable solvents for this reaction include toluene. However, where the base is a liquid, the reaction may advantageously be carried out using the neat base as a solvent. Preferably, the reaction is carried out in pyridine.

The reaction may be carried out using staged process conditions to optimise conversion of the compound of Formula (I) to citalopram. Thus, for example, the reaction temperature can be staged so that the reaction is initially carried out at a first temperature of 5 to 40° C. preferably 15 to 30° C. and subsequently maintained at a second temperature of 50 to 100 C, preferably 80 to 90° C.

In a preferred embodiment, the reaction is carried out in a staged process comprising the initial reaction of the compound of Formula (I) with thionyl chloride, in the presence of a base at a temperature range of 5–40° C., preferably 15–30° C. for a period of from 0.5 to 4 hours, preferably 1–3 hours, followed by the addition of phosphorus oxychloride, the mixture being heated to a temperature range of from 50–100° C., preferably 80–90° C. for a period 3–6 hours, preferably 4–5 hours. Where, for example, phosphorus oxychloride is used as the sole reactant, the reaction conditions can be similarly staged.

The invention further provides the use of a compound of Formula (I) as defined above in a one-pot process for the synthesis of citalopram. Preferably the group R in the compound of Formula (I) represents a $C_2$ or $C_3$ alkylene group which may be unsubstituted or substituted by one or more groups selected from $C_1$ to $C_6$ alkyl (which may be unsubstituted or substituted by halo, $C_1$ to $C_6$ alkoxy, or $C_6$ to $C_{15}$ aryl), $C_5$ to $C_{10}$ cycloalkyl (which may be unsubstituted or substituted by halo, $C_1$ to $C_6$ alkyl, $C_1$ to $C_6$ alkoxy, or $C_6$ to $C_{15}$ aryl) or $C_6$ to $C_{15}$ aryl (which may be unsubstituted or substituted by halo, $C_1$ to $C_6$ alkoxy or $C_1$ to $C_6$ alkyl). More preferably the compound of Formula (I) has the structure:

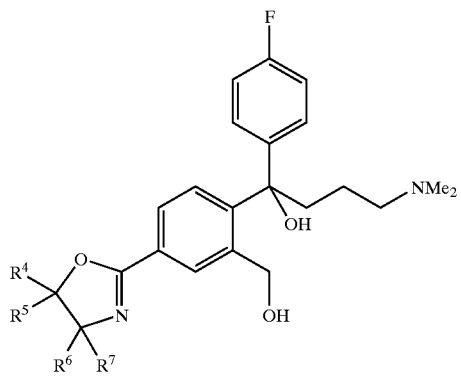

wherein $R^4$, $R^5$, $R^6$ and $R^7$ each independently represents H, $C_1$ to $C_8$ alkyl, $C_5$ to $C_{10}$ cycloalkyl or aryl. Preferably $R^6$ and $R^7$ each independently represents H or $C_1$ to $C_8$ alkyl and even more preferably, $R^4$ and $R^5$ both represent H, and $R^6$ and $R^7$ both represent methyl.

The invention also provides a novel compound having the Formula (I)

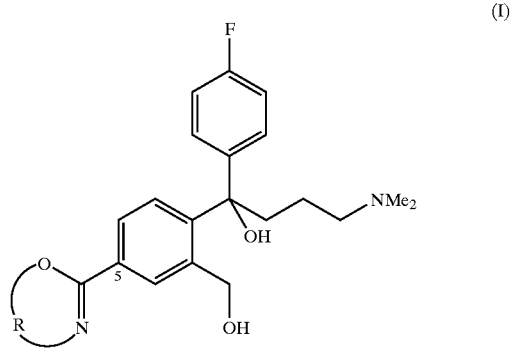

(I)

wherein R represents a $C_2$ to $C_5$ alkylene group which may be unsubstituted or substituted by one or more of the groups selected from $C_1$ to $C_8$ alkyl, $C_8$ to $C_{15}$ aryl, $C_8$ to $C_{15}$ heteroaryl, $C_3$ to $C_{10}$ cycloalkyl, $C_5$ to $C_{10}$ heterocycloalkyl, $C_7$ to $C_{10}$ aralkyl, $C_1$ to $C_6$ alkoxy, or a $C_3$ to $C_7$ cycloalkyl group attached to the alkylene group via a spiro carbon atom, or the alkylene group may contain a $C_8$–$C_{15}$ aryl group fused to two alkylene carbon atoms.

Particularly preferred novel compounds of the present invention are the compounds of Formula (I) wherein R represents a $C_2$ to $C_5$ alkylene group which may be unsubstituted or substituted by one or more of the groups selected from $C_5$ to $C_{10}$ cycloalkyl, $C_5$ to $C_{10}$ heterocycloalkyl, $C_7$ to $C_{10}$ aralkyl, $C_1$ to $C_5$ alkoxy, or a $C_5$ to $C_7$ cycloalkyl group attached to the alkylene group via a spiro carbon atom, or the alkylene group may contain a $C_5$–$C_{15}$ aryl group fused to two alkylene carbon atoms.

The invention also provides the use of these novel compounds in the synthesis of citalopram.

Preferably, in the novel compounds of the present invention, R represents a $C_2$ to $C_5$ alkylene group substituted by $C_5$ to $C_8$ cycloalkyl, $C_1$ to $C_6$ alkoxy, or a benzene or naphthalene ring fused to two carbon atoms of the alkylene group.

Typically, the compound of Formula (I) is prepared from 5-carboxyphthalide, which is commercially available, or may be prepared by reaction of terephthalic acid with trioxane in 30% oleum (L. S. Forney, J. Org. Chem. 35, No. 5, p. 1695 (May 1970). The 5-carboxyphthalide can be reacted with the appropriate amino alcohol to form an amide alcohol Intermediate which is subsequently cyclised to form the compound of Formula (I). By way of an illustrative example, the compound of Formula (I) having the structure:

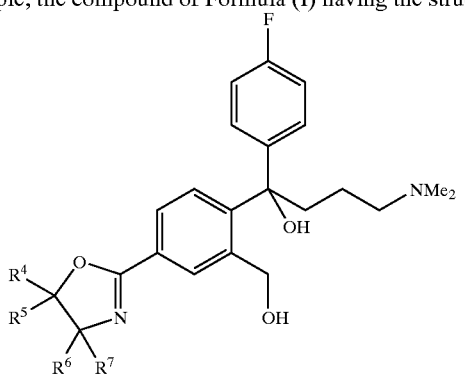

can be formed from the reaction of 5-carboxyphthalide with an amino alcohol of th Formula:

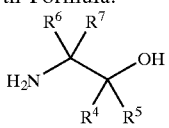

to form the amide alcohol:

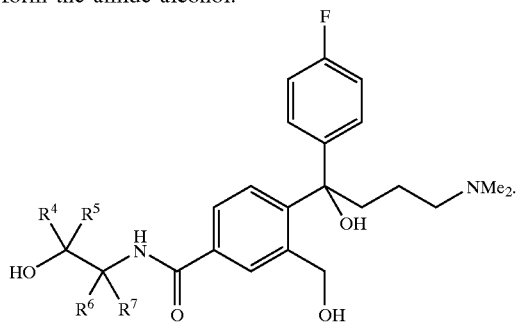

The amide alcohol is subsequently subjected to a cyclisation reaction to form the compound of Formula (I).

It will be appreciated that the nature of the C-5 substituent in the above process is dependent upon the structure of the amino alcohol that is condensed with the carboxyl group of 5-carboxyphthalide. Suitable amino alcohols that may be used to form the compounds of Formula (I) include 2-amino-3-methylphenol, 2-amino-1-hexanol, 2-amino-3-methylbenzyl alcohol, 1-aminomethyl-1-cyclohexanol, (S)-(−)-2-amino-3-phenyl-1-propanol. A particularly preferred amino alcohol is 2-amino-2-methyl propanol.

The following scheme illustrates a procedure for the preparation of the 4,4-dimethyl-4,5-dihydrol-1,3oxazol-2-yl substituted phthalide:

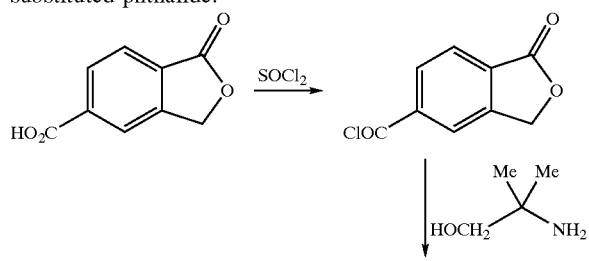

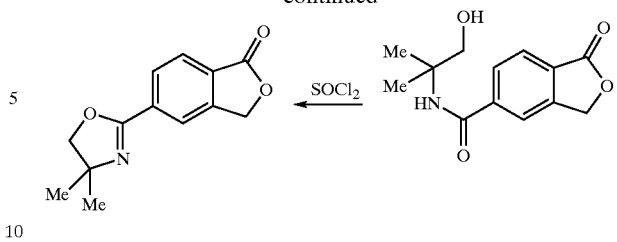

As indicated in the above scheme, 5-carboxyphthalide is converted to the corresponding acid chloride using thionyl chloride. Reaction of the acid chloride with the amino alcohol, 2-methyl-2-aminopropanol, forms an amide alcohol intermediate, which can be cyclised using thionyl chloride to form the corresponding 5-oxazoline substituted phthalide.

The oxazoline phthalide may be converted to the intermediate of Formula (I) by two successive Grignard reactions in accordance with known literature procedures.

As used herein the term "alkyl" refers to $C_1$ to $C_{20}$, preferably $C_1$ to $C_6$ straight or branched carbon chains. Particularly preferred alkyl groups for the compounds and methods of the invention include methyl, ethyl, propyl, isopropyl, butyl, and tertiary butyl.

The term "$C_2$ to $C_5$ alkylene group" refers to a —$(CH_2)_n$— moiety wherein n represents 2, 3, 4 or 5. Particularly preferred alkylene groups for the compounds and methods of the invention include ethylene, propylene and butylene. Ethylene is an especially preferred group.

The term "substituted alkyl" refers to $C_1$ to $C_{20}$, preferably $C_1$ to $C_6$ straight or branched carbon chains as defined above, in which one or more hydrogen atoms are substituted with halo, $C_1$ to $C_6$ alkoxy, or $C_6$–$C_{15}$ aryl as defined below. Particularly preferred substituted alkyl groups for the compounds and methods of the invention include halo-, methoxy-, or phenyl-substituted methyl, ethyl, propyl groups.

The term "aryl" represents a carbocyclic group containing from six to fifteen carbon atoms and having at least one aromatic ring. Particularly preferred aryl groups for the compounds and methods of the present invention include phenyl and naphthyl.

The term "substituted aryl" refers to aryl groups containing from six to fifteen carbon atoms with all available substitutable carbon atoms of the carbocyclic group being intended as possible points of attachment, said carbocyclic group being optionally substituted with one or more of halo, $C_1$ to $C_6$ alkyl, or $C_1$ to $C_6$ alkoxy. Particularly preferred substituted aryl groups for the compounds and methods of the present invention include halo- and methoxy-substituted phenyl and naphthyl.

The term "heteroaryl" refers to aryl groups as defined above wherein one or more carbon atoms of the ring are replaced by N or S. Particularly preferred heteroaryl groups for the compounds and methods of the invention include pyridyl, quinolyl and imidazolyl.

The term "alkoxy" refers the group —O-alkyl, wherein alkyl is as defined above. Particularly preferred alkoxy groups for the. compounds and methods of the present invention include methoxy, ethoxy, butoxy, isopropyloxy and tert-butyloxy.

The "aralkyl" refers to an alkyl group as defined above wherein one or more hydrogen atoms have been replaced by substituted or unsubstituted aryl groups as defined above. An preferred aralkyl group for the compounds and methods of the invention is benzyl.

The term "cycloalkyl" refers to saturated carbocyclic rings, containing from 3 to 20, preferably 3 to 7, carbon atoms. Particularly preferred cycloalkyl groups for the compounds and methods of the invention include cyclopropyl, cyclobutyl, cyclopentyl and cyclohexyl.

The term "substituted cycloalkyl" refers to cycloalkyl as defined above wherein one or more of the hydrogen atoms are substituted with any of the groups halo, $C_1$ to $C_6$ alkyl and $C_1$ to $C_6$ alkoxy as defined above. Particularly preferred substituted cycloalkyl groups for the compounds and methods of the present invention include halo-, $C_1$ to $C_6$ alkyl- and $C_1$ to $C_6$-alkoxy-substituted cyclopropane, cyclobutane, cyclopentane and cyclohexane.

The term "heterocycloalkyl" refers to $C_5$ to $C_{10}$ cycloalkyl groups wherein one or more of the carbon atoms are replaced by a heteroatom N, O or S. Particularly preferred heterocycloalkyl groups for the compounds and methods of the invention include piperidinyl, piperazinyl, tetrahydrofuranyl and morpholinyl.

The term "halo" refers to fluoro, chloro, bromo or iodo.

Where the $C_3$ to $C_7$ cycloalkyl groups are linked to an alkylene carbon atoms of the R group via a spiro carbon, preferred groups for the compounds and methods of the invention include spiro-cyclohexyl and spiro-cyclopentyl.

Where the $C_6$ to $C_{15}$ aryl group is fused to two alkylene carbon atoms of the R group, preferred aryl groups for the compounds and methods of the invention include benzyl and naphthalenyl.

The following Examples and Scheme illustrate a typical procedure for the preparation of citalopram in accordance with aspects of the present invention.

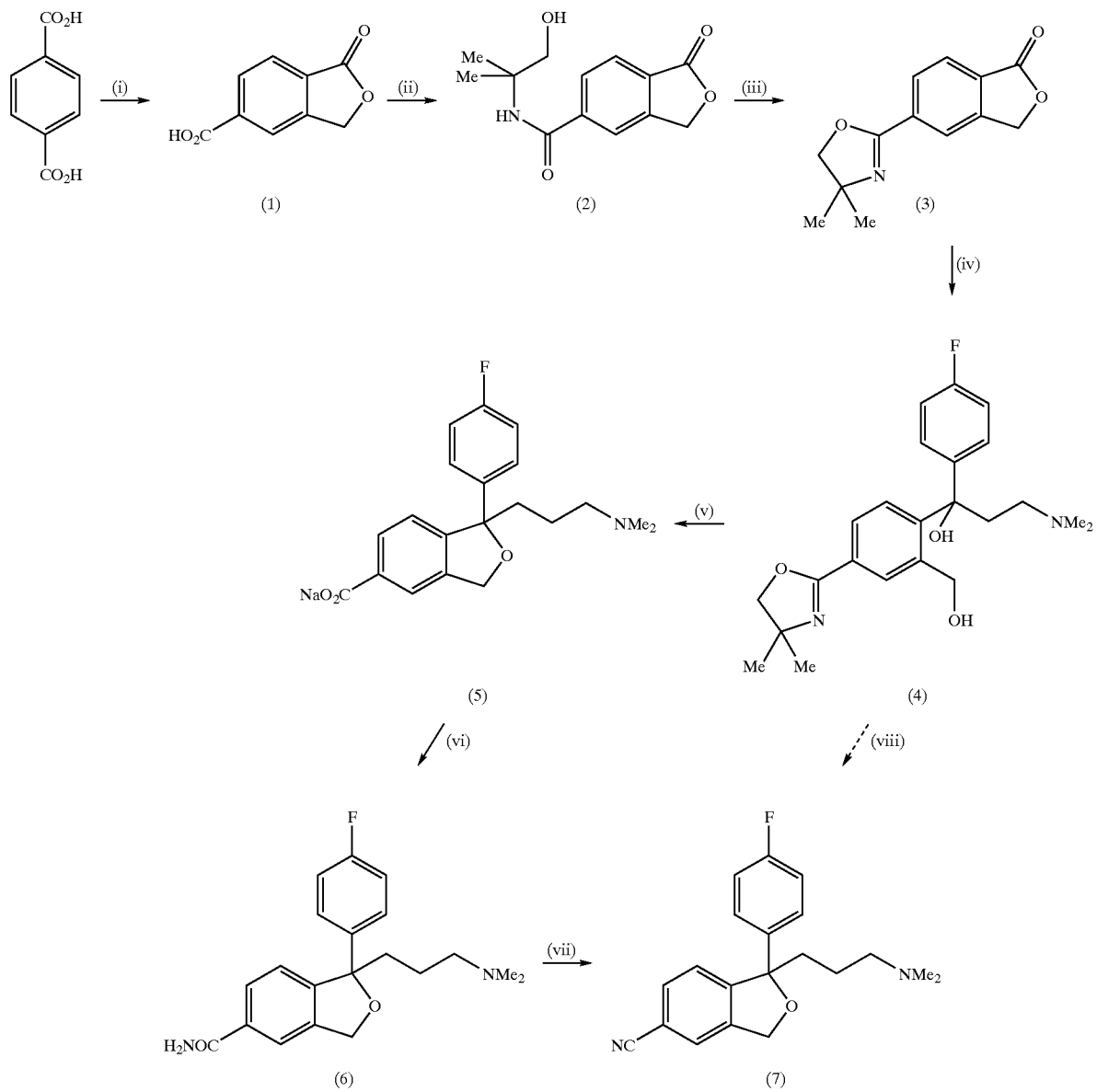

Key to steps: (i) trioxane, oleum; (ii) (a) thionyl chloride, DMF, (b) 2-amino-2-methyl-propanol; (iii) thionyl chloride, (iv) (a) MgBr—$C_6H_4$—F, (b) MgBr$(CH_2)_3$NMe$_2$, (v) (a) H$_2$SO$_4$ (aq.), (b) NaOH(aq.); (vi) thionyl chloride, NH$_3$ (g), (vii) POCl$_3$, (viii) SOCl$_2$, POCl$_3$

EXAMPLES

I. Preparation of Phthalide Acid (1)

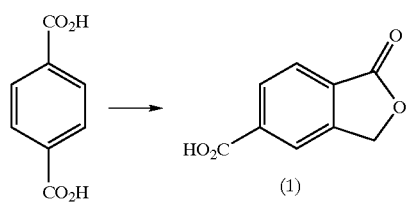

Terephthalic acid was suspended in 25–30% oleum. Trioxane was added and the mixture was heated to 140–150° C. for 4–8 hours. The reaction mixture was cooled and then quenched by cautious addition of water at less than 80° C. The resulting suspension was cooled to about 40° C. and the solid was filtered off. The filter cake was washed with water followed by propan-2-ol before slurrying the solid in propan-2-ol at reflux for 30 minutes. After cooling to 20–25° C. the product was filtered off, washed with propan-2-ol and dried at 60–70° C. under reduced pressure.

II. Preparation of Hydroxy Amide (2)

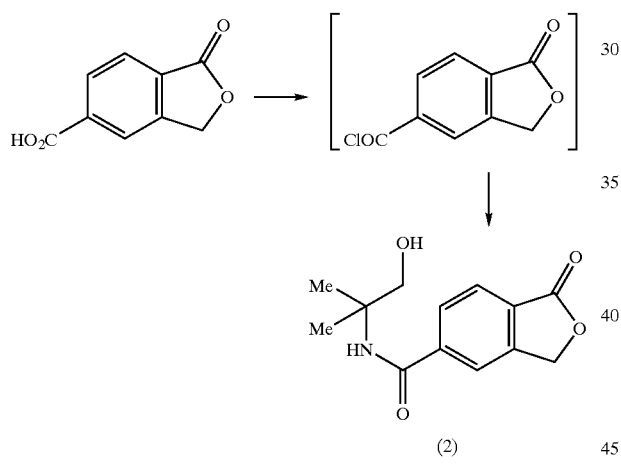

The phthalide acid (1) (900 g) was suspended in 5 volumes of toluene containing a catalytic amount of DMF. The mixture was heated to 70–80° C. and thionyl chloride (734 g) was added slowly to the mixture at less than 80° C. The mixture was heated for 1 hour at reflux. The resultant solution was concentrated by distillation at atmospheric pressure and cooled to about 75° C. Dimethylformamide was added slowly and the mixture was cooled to approximately 20° C. This solution was added at 15–20° C. to a solution of 2-amino-2-methyl propanol (993 g) in toluene (1.6 kg). After the addition was complete, the solution was stirred for 30 minutes and the pH adjusted to 2–3 by slow addition of hydrochloric acid. The mixture was stirred at 15–20° C. for one hour. The precipitated product was filtered off, washed with water, and dried at about 60° C. under reduced pressure.

$^1$H NMR (CDCl$_3$, 270 MHz): 1.6 (6H, s), 4.0 (2H, s), 5.4 (2H, s), 6.1 (1H, br), 7.8–8.1 (2H, m).

III. Preparation of Oxazolin (3)

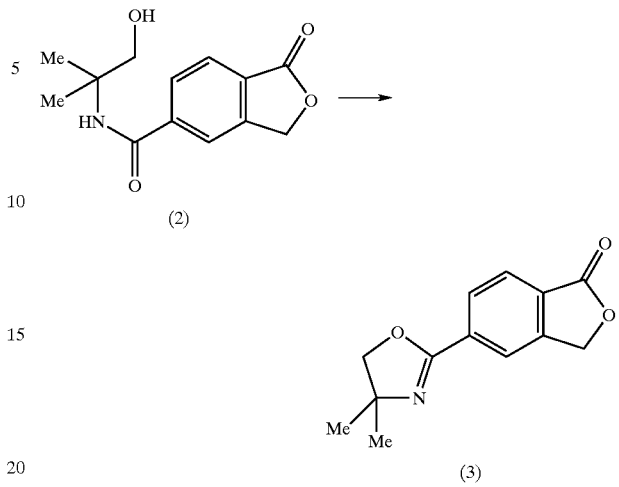

The hydroxy amide (2) (1.0 kg) was suspended in 4 volumes of dichloromethane and thionyl chloride (0.502 kg) was added at 20–25° C. After stirring for 1 hour at 20–25° C. methanol was added, and the mixture stirred at ambient temperature for 30 minutes. Triethylamine was added to neutralise the mixture to pH 4–5. Water was then added, and the layers allowed to separate. The organic extracts were washed with water and the dichloromethane was distilled off before the addition of toluene. The resulting mixture was filtered at 60–70° C. Heptane was added and the solution heated to reflux. After cooling to 15–20° C. the product was filtered off, washed with heptane and dried at 50° C. under reduced pressure.

$^1$H NMR (CDCl$_3$, 270 MHz): 1.5 (6H, s), 4.2 (2H, s), 5.3 (2H, s), 8.0 (1H, d), 8.1 (1H, d).

IV. Preparation of the Oxazoline Diol (4)

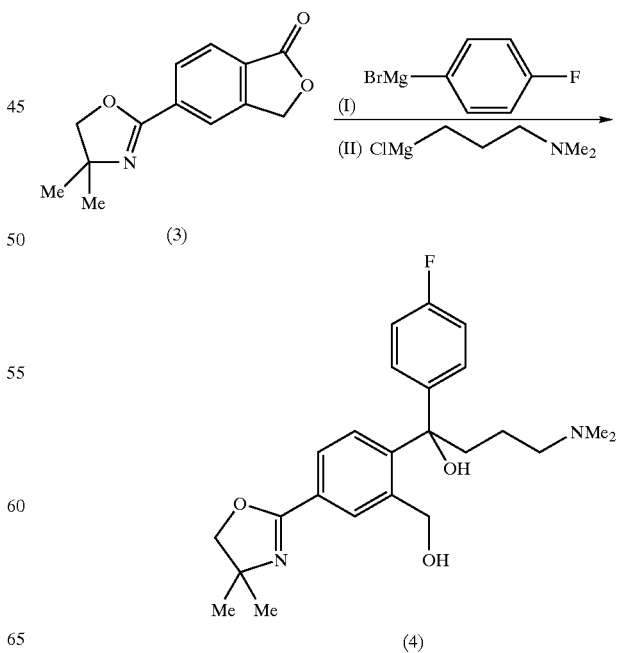

Preparation of Grignard Reagents:

(I) Aromatic Grignard Reagent 1-bromo-4-fluorobenzene was added at reflux to a suspension of magnesium in tetrahydrofuran (containing a catalytic amount of iodine) under a nitrogen atmosphere. The reflux was continued for 30 minutes after completion of the addition. The reaction mixture was then allowed to cool and was then ready for use.

(II) Aliphatic Grignard Reagent

A solution of 3-dimethylaminopropyl chloride hydrochloride in water/toluene was basified by the addition of sodium hydroxide solution. The layers were separated and the aqueous layer was extracted with toluene. The combined toluene phases were washed with water and dried by azeotropic distillation in vacuo at less than 35° C. The solution was then diluted with tetrahydrofuran. A portion of this solution was added to magnesium and a catalytic quantity of 1,2-dibromoethane under a nitrogen atmosphere. The mixture was heated to reflux to initiate the reaction, and one the initial exotherm had subsided, the remaining THF solution prepared above was added at a steady constant rate so that the mixture was maintained at reflux. After the addition was complete the mixture was held at reflux for a further 15 minutes, before cooling to ambient temperature ready for use.

The oxazoline (3) (494 g) was suspended in 3 volumes of THF under a nitrogen atmosphere. The aromatic Grignard reagent perpared in step (i) (1.94 liters, 1.2 mol in THF) was added slowly to the mixture at a temperature of 20–30° C. The aliphatic Grignard perpared in step (ii) (3.0 liters, 0.856 mol in THF) was then added at a temperature of 20–30° C. The mixture was stirred at this temperature for 30 minutes. After evaporation of the solvent, the reaction was quenched by the addition of water at 20–30° C. Toluene was added and the mixture acidified to pH 1.5–1.9 with hydrochloric acid. The layers were separated and the aqueous layer was collected and washed with toluene. Toluene was added to the aqueous solution and the mixture basified to pH 9–10 by the addition of aqueous ammonia. The layers were separated and the aqueous phase was extracted with toluene. The combine toluene phases were cooled to 10–15° C., and the mixture stirred for approximately 10 hours before further cooling to between −10 to −5° C. for 2 hours. The precipitate was filtered off, washed with cold toluene followed by heptane and the product dried at 45–55° C. $^1$H NMR (CDCl$_3$, 270 MHz): 1.4 (6H, s), 1.5–1.8 (2H, m), 2.2 (6H, s) 2.2–2.7 (4H, m), 4.1 (2H, s), 4.2 (1H, d), 4.4 (1H, d), 7.0 (2H, m), 7.3 (2H, m), 7.5 (1H, m), 7.9 (2H, m), V. Preparation of Diol Acid (5)

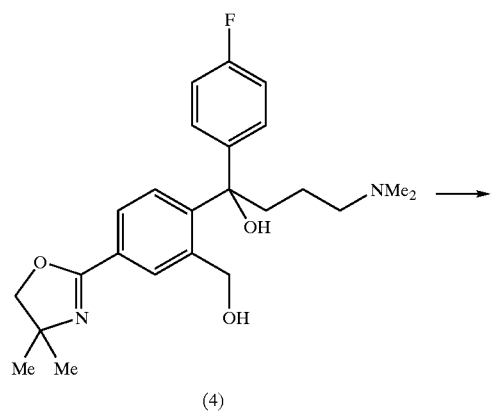

(4)

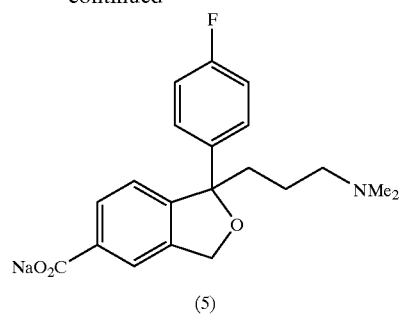

(5)

The oxazoline diol (4) (500 g) was dissolved In aqueous sulphuric acid (2.862 kg. 12.4%) and the mixture was heated to reflux for 2 hours. The mixture was made basic with sodium hydroxide and the amino alcohol was removed by co-distillation with water. The aqueous solution was dried by azeotropic distillation with toluene and the resultant toluene mixture was filtered to remove inorganic salts. Concentration under vacuum yielded the acid sodium salt (5) as a gelatinous solid containing approximately 15% solvent (100%, mp.—decomposes above 200° C.).

$^1$H NMR (MeOH-d$_4$, 270 MHz): 1.2 (2H, m), 2–2.4 (10H, m), 5.2 (2H, s), 7.0 (2H, dd), 7.4 (1H, d), 7.55 (2H, m), 7.8 (1H, s), 7.9 (1H, d).

VI. Preparation of Amide (6)

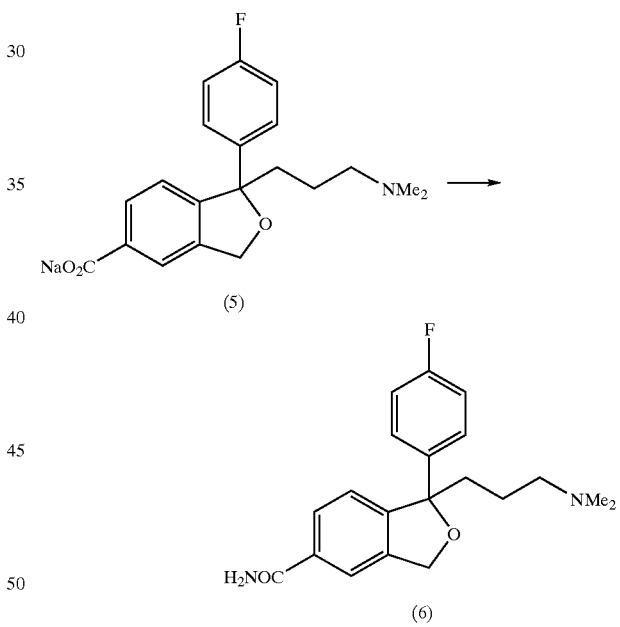

The acid (5) (533 g) was dissolved in warm CH$_2$Cl$_2$ and was added to a solution of thionyl chloride (520 g in 0.71 kg dichloromethane) at 25° C. After 15 minutes, the resultant cloudy solution was cooled to 4° C. and ammonia gas was added until the mixture was basic. The resultant suspension was quenched with water, warmed and the organic layer separated. The aqueous layer was extracted with 2×1 volume of CH$_2$Cl$_2$ and the combined organic layers were washed several times with warm Na$_2$CO$_3$ solution and water to remove unreacted acid. The organic layer was dried, the solvent evaporated and the product (6) isolated by filtration (45%, mp. 126.4° C.). Further material may be isolated from the liquors.

$^1$H NMR (CDCl$_3$, 270 MHz): 1.2 (2H, m), 2.1–2.3 (10H, m), 5.2 (2H, dd), 6.3 (2H, br), 7.0 (2H, dd), 7.3 (1H, d), 7.5 (2H, m), 7.7 (1H, s), 7.75 (1H, d).

VII. Preparation of Citalopram (7)

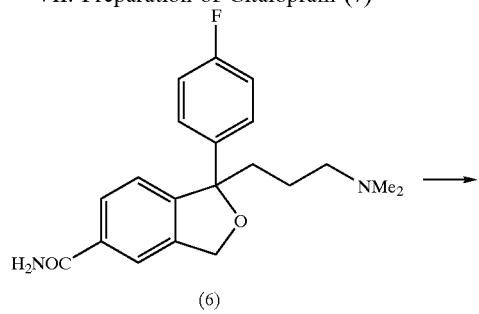

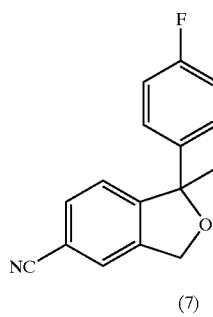

The amide (6) (257 g) was suspended in acetonitrile (1.02 kg) and heated to 60° C. Phosphorous oxychloride (115 g) was added at such a rate so as to maintain the reaction mixture at reflux. After completion, the reaction mixture was cooled to 0° C. and quenched by the addition of 20% sodium carbonate. The precipitated salts were removed by filtration and the aqueous acetonitrile was distilled under vacuum. The resultant aqueous mixture was extracted with ethyl acetate and treated with activated carbon. Concentration of the solvent under vacuum yielded the product (7) as a viscous oil (92%).

VIII. Conversion of Citalopram Free Base to Hydrobromide Salt

Citalopram free base (7) (393 g) was dissolved in 5 volumes of acetone and 10% of the solution was reserved. The bulk of the acetone solution was cooled to 0° C. under nitrogen. Hydrogen bromide gas was introduced keeping the temperature below 10° C. The reserve solution of free base was used to adjust the solution pH to 7 if necessary. The precipitated salt was collected by filtration and washed with acetone. The mother liquors were concentrated to give a second crop of product.

IX. One-Pot Process for Preparation of Citalopram

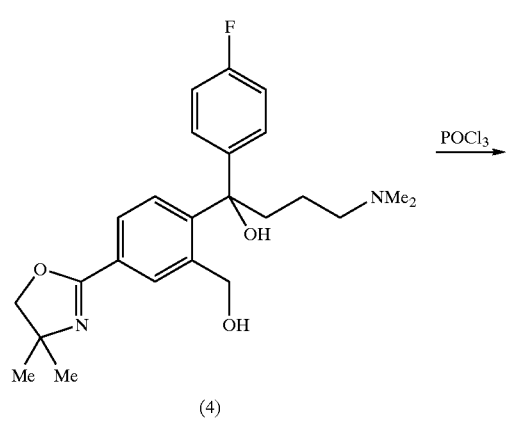

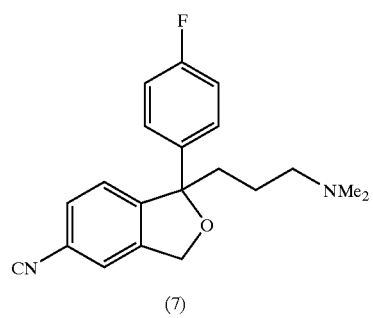

The oxazoline diol (4) (3 molar equivalents) was dissolved in pyridine (5 volumes) and POCl$_3$ (3 molar equivalents) was added. The reaction mixture was stirred for 1 hour at 20–25° C. The mixture was heated to 80–90° C. for 4 hours. The reaction mixture was quenched with water, extracted into toluene and evaporated to dryness (38%).

X. One-Pot Process for Preparation of Citalopram

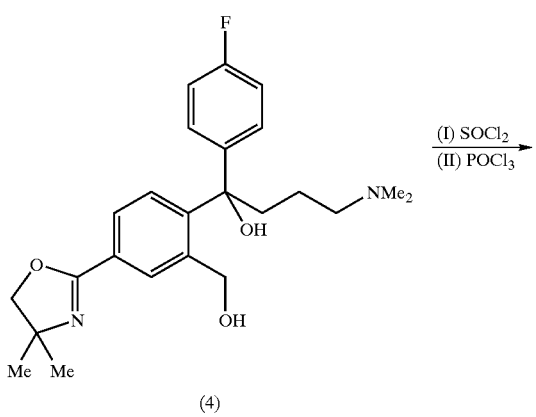

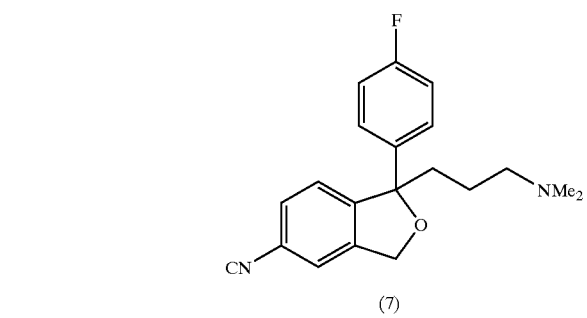

The oxazoline diol (4) (1.5 molar equivalents) was dissolved in pyridine (5 volumes) and thionyl chloride (1.5 molar equivalents) was added. The mixture was stirred at 20–25° C. for 1 hour. Phosphoryl chloride (2 molar equivalents) was added and the mixture maintained with stirring for 4 hours. The reaction mixture was quenched with water, extracted into toluene and evaporated to dryness (48%).

What is claimed is:

1. A process for the synthesis of citalopram comprising:

(a) converting a compound of Formula (I):

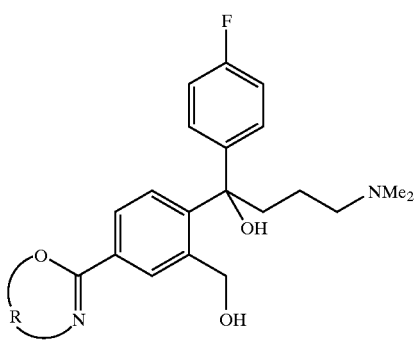

(I)

wherein R represents a $C_2$ to $C_5$ alkylene group which may be unsubstituted or substituted by one or more of the groups selected from: $C_1$ to $C_6$ alkyl, which may be unsubstituted or substituted by halo, $C_1$ to $C_6$ alkoxy, or $C_6$ to $C_{15}$ aryl; $C_3$ to $C_{10}$ cycloalkyl, which may be unsubstituted or substituted by halo, $C_1$ to $C_6$ alkyl, $C_1$ to $C_6$ alkoxy, or $C_6$ to $C_{15}$ aryl; $C_5$ to $C_{10}$ heterocycloalkyl; $C_6$–$C_{15}$ aryl, which may be unsubstituted or substituted by halo, $C_1$ to $C_6$ alkoxy, or $C_1$ to $C_6$ alkyl; $C_7$ to $C_{10}$ aralkyl; $C_1$ to $C_6$ alkoxy and heteroaryl; or the alkylene group can be substituted by one or more $C_3$ to $C_7$ cycloalkyl groups attached to the alkylene group via a spiro-carbon atom; or the alkylene group may contain a $C_6$–$C_{15}$ aryl group fused to two alkylene carbon atoms;

to a compound of Formula (II):

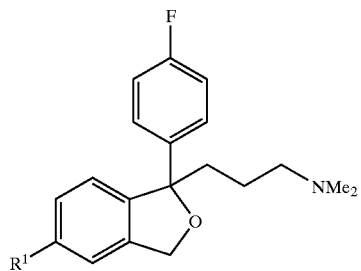

(II)

wherein $R^1$ represents a carboxylic acid group or a salt or an ester thereof, and (b) converting the compound of Formula (II) to form citalopram or a pharmaceutically acceptable salt thereof.

2. A process according to claim 1 wherein the compound of Formula (II) is formed by subjecting the compound of Formula (I) to a one-pot cyclisation-hydrolysis reaction.

3. A process according to claim 1 wherein the compound of Formula (II) wherein $R^1$ represents an acid or salt thereof is formed by subjecting the compound of Formula (I) to acid hydrolysis followed by reaction with a base.

4. A process according to claim 1 wherein the compound of Formula (II) is formed by:

(i) subjecting the compound of Formula (I) to reaction with a mineral acid to form an amino ester intermediate, and (ii) subjecting the amino ester intermediate to reaction with a base.

5. A process according to claim 1 wherein the compound of Formula (II) wherein $R^1$ represents an ester is formed by subjecting the compound of Formula (I) to acid hydrolysis in the presence of an alcohol.

6. A process according to claim 1 wherein the acid hydrolysis is carried out using a mineral acid.

7. A process according to claim 1 wherein the acid hydrolysis is carried out using a mineral acid selected from the group consisting of hydrochloric acid, hydrobromic acid, sulfuric acid and phosphoric acid.

8. A process according to claim 1 wherein the compound of Formula (II), wherein $R^1$ represents an acid or salt thereof, is formed by subjecting the compound of Formula (I) to acid hydrolysis followed by reaction with a base, wherein the base is selected from the group consisting of lithium hydroxide, sodium hydroxide and potassium hydroxide.

9. A process according to claim 1 wherein the compound of Formula (II) is formed by subjecting the compound of Formula (I) to an acid hydrolysis reaction with sulfuric acid, followed by reaction with sodium hydroxide.

10. A process for the synthesis of citalopram comprising:

(a) converting a compound of Formula (I):

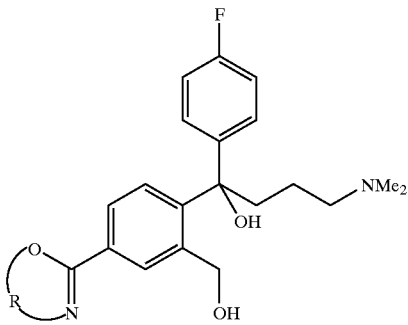

(I)

wherein R represents a $C_2$ to $C_5$ alkylene group which may be unsubstituted or substituted by one or more of the groups selected from: $C_1$ to $C_6$ alkyl, which may be unsubstituted or substituted by halo, $C_1$ to $C_6$ alkoxy, or $C_6$ to $C_{15}$ aryl; $C_3$ to $C_{10}$ cycloalkyl, which may be unsubstituted or substituted by halo, $C_1$ to $C_6$ alkyl, $C_1$ to $C_6$ alkoxy, or $C_6$ to $C_{15}$ aryl; $C_5$ to $C_{10}$ heterocycloalkyl; $C_6$–$C_{15}$ aryl, which may be unsubstituted or substituted by halo, $C_1$ to $C_6$ alkoxy, or $C_1$ to $C_6$ alkyl; $C_7$ to $C_{10}$ aralkyl; $C_1$ to $C_6$ alkoxy and heteroaryl; or the alkylene group can be substituted by one or more $C_3$ to $C_7$ cycloalkyl groups attached to the alkylene group via a spiro-carbon atom; or the alkylene group may contain a $C_6$–$C_{15}$ aryl group fused to two alkylene carbon atoms;

to a compound of Formula (II):

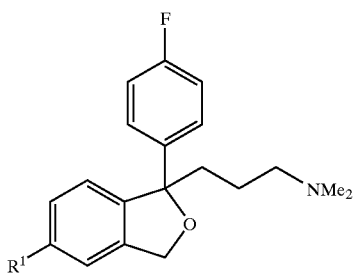

(II)

wherein $R^1$ represents a carboxylic acid group or a salt or an ester thereof, and (b) converting the compound of Formula (II) to form citalopram or a pharmaceutically acceptable salt thereof wherein said step (b) is carried out via an amide intermediate of Formula (III).

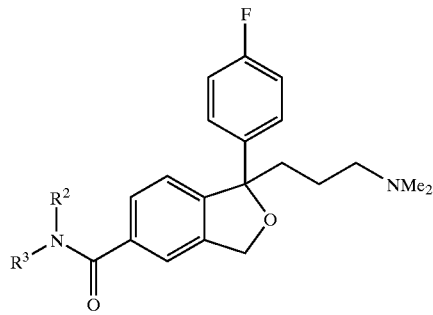

wherein $R^2$ and $R^3$ independently represent H or $C_1$ to $C_6$ alkyl, $C_5$ to $C_{10}$ cycloalkyl, aralkyl or aryl.

11. A process according to claim 10 wherein $R^2$ and $R^3$ each independently represents H or $^t$Bu.

12. A process according to claim 10 wherein $R^2$ and $R^3$ both represent H or both represent $^t$Bu.

13. A process according to claim 10 wherein one of $R^2$ and $R^3$ represents H and the other represents $^t$Bu.

14. A process according to claim 10 wherein the amide of Formula (III) is formed by:
   (i) converting the compound of Formula (II) wherein $R^1$ represents a carboxylic acid or a salt thereof, to an acid chloride, —COCl; and
   (ii) converting the acid chloride to the group —C(O)NR$^2$R$^3$, wherein $R^2$ and $R^3$ are as defined in claim 10.

15. A process according to claim 10 wherein the amide of Formula (III) is formed by:
   (i) subjecting the compound of Formula (II) wherein $R^1$ represents a carboxylic acid or a salt thereof, to reaction with a reagent selected from the group consisting of: thionyl chloride, PCl$_3$, POCl$_3$, PCl$_5$, oxalyl chloride and a mixture of carbon tetrachloride-triphenylphosphine; and
   (ii) converting the acid chloride to the group —C(O)NR$^2$R$^3$.

16. A process according to claim 10 wherein the amide of Formula (III) is formed by:
   (i) converting the compound of Formula (II) wherein $R^1$ represents a carboxylic acid or a salt thereof to an acid chloride, —COCl; and
   (ii) subjecting the acid chloride to reaction with ammonia or an amine HNR$^2$R$^3$.

17. A process according to claim 10 wherein the amide of Formula (III) is formed by aminolysis of the compound of Formula (II) wherein $R^1$ represents a carboxylic ester group.

18. A process according to claim 10 wherein the amid of Formula (III) is converted to citalopram by reaction with a dehydrating agent.

19. A process according to claim 10 wherein amide of Formula (II) is converted to citalopram by reaction with a dehydrating agent selected from the group consisting of SOCl$_2$, P$_2$O$_5$, POCl$_3$, PCl$_5$ and HMPA.

20. A process for the preparation of citalopram comprising the steps of:
   (a) subjecting the compound of Formula (I) having the structure:

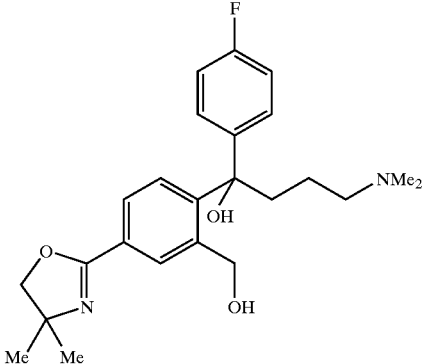

to a ring-closure reaction with aqueous sulfuric acid followed by a hydrolysis reaction with aqueous sodium hydroxide to produce a compound of formula (II) having the structure:

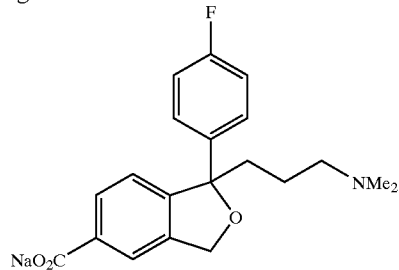

(b) subjecting the compound of Formula (II) to reaction with thionyl chloride followed by reaction with ammonia to form the compound of Formula (III) having the structure:

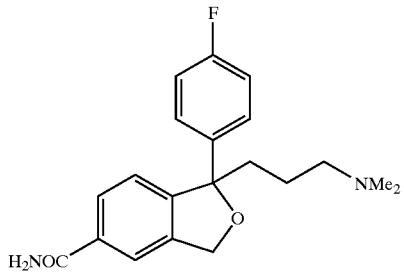

(c) subjecting the compound of Formula (III) to a reaction with POCl$_3$ to form citalopram.

21. A process according to claim 20 wherein step (b) is carried out as a one-pot procedure.

22. A process according to claim 1 wherein the group R in Formula (I) represents a $C_2$ or $C_3$ alkylene group which may be unsubstituted or substituted by one or more groups selected from $C_1$ to $C_6$ alkyl; which may be unsubstituted or substituted by halo, $C_1$ to $C_6$ alkoxy, or $C_6$ to $C_{15}$ aryl, $C_5$ to $C_{10}$ cycloalkyl; which may be unsubstituted or substituted by halo, $C_1$ to $C_6$ alkyl, $C_1$ to $C_6$ alkoxy, or $C_6$ to $C_{15}$ aryl; or $C_6$ to $C_{15}$ aryl, which may be unsubstituted or substituted by halo; $C_1$ to $C_6$ alkoxy, or $C_1$ to $C_6$ alkyl).

23. A process according to claim 1 wherein the compound of Formula (I) represents:

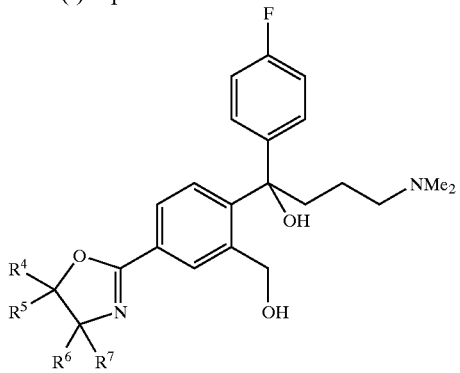

wherein $R^4$, $R^5$, $R^6$ and $R^7$ each independently represents H, $C_1$ to $C_6$ alkyl, which may be unsubstituted or substituted by halo, $C_1$ to $C_6$ alkoxy, or $C_6$ to $C_{15}$ aryl; $C_5$ to $C_{10}$ cycloalkyl, which may be unsubstituted or substituted by halo, $C_1$ to $C_6$ alkyl, $C_1$ to $C_6$ alkoxy, or $C_6$ to $C_{15}$ aryl; $C_1$ to $C_6$ alkoxy; or one of $R^4$ or $R^5$ taken together with one of the $R^6$ or $R^7$ groups form a benzene ring fused to the ethylene carbon atoms of the oxazoline ring; or one or both of the $R^4$ and $R^5$ or $R^6$ and $R^7$ groups taken together represents a $C_3$–$C_8$ cycloalkyl group attached to one or both of the oxazoline ethylene carbon atoms via a spiro carbon.

24. A process according to claim 1 wherein the compound of Formula (I) represents:

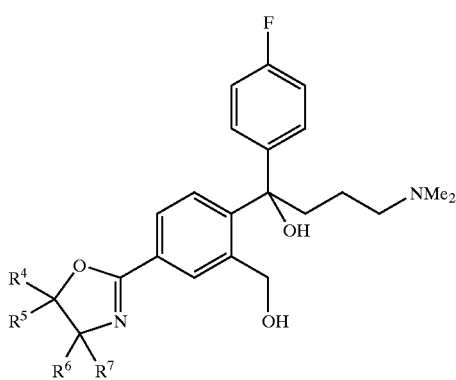

wherein $R^4$, $R^5$, $R^6$ and $R^7$ each independently represents H, $C_1$ to $C_6$ alkyl, $C_5$ to $C_{10}$ cycloalkyl or $C_6$ to $C_{15}$ aryl.

25. A process according to claim 1 wherein the compound of Formula (I) represents

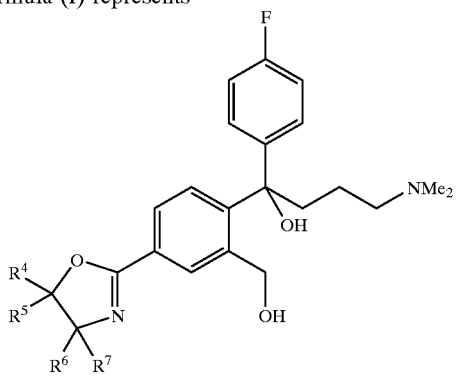

wherein $R^4$ and $R^5$ each independently represent H, $C_1$ to $C_6$ alkyl, $C_5$ to $C_{10}$ cycloalkyl or $C_6$ to $C_{15}$ aryl; and $R^6$ and $R^7$ each independently represent H or $C_1$ to $C_6$ alkyl.

26. A process according to claim 1 wherein the compound of Formula (I) represents:

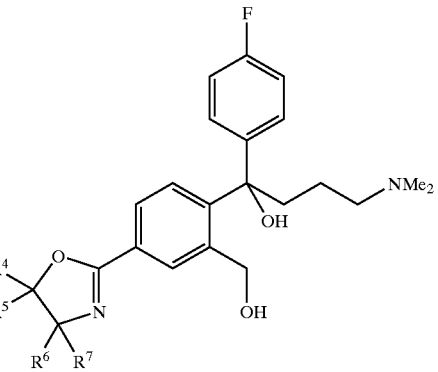

wherein $R^4$ and $R^5$ both represent H and $R^6$ and $R^7$ both represent methyl.

27. A process for the direct conversion of a compound of Formula (I):

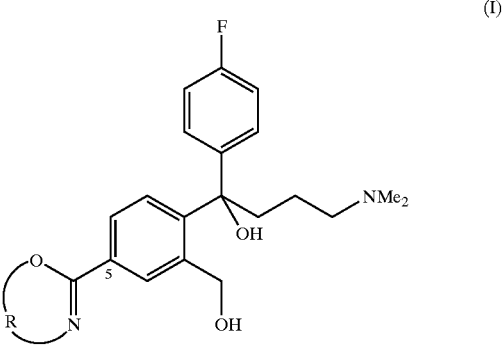

wherein R represents a $C_2$ to $C_5$ alkylene group which may be unsubstituted or substituted by one or more of the groups selected from: $C_1$ to $C_6$ alkyl, which may be unsubstituted or substituted by halo, $C_1$ to $C_6$ alkoxy, or $C_6$ to $C_{15}$ aryl; $C_3$ to $C_{10}$ cycloalkyl, which may be unsubstituted or substituted by halo, $C_1$ to $C_6$ alkyl, $C_1$ to $C_6$ alkoxy, or $C_6$ to $C_{15}$ aryl; $C_5$ to $C_{10}$ heterocycloalkyl; $C_6$–$C_{15}$ aryl, which may be unsubstituted or substituted by halo, $C_1$ to $C_6$ alkoxy, or $C_1$ to $C_6$ alkyl; $C_7$ to $C_{10}$ aralkyl; $C_1$ to $C_6$ alkoxy and heteroaryl; or the alkylene group can be substituted by one or more $C_3$ to $C_7$ cycloalkyl groups attached to the alkylene group via a spiro-carbon atom; or the alkylene group may contain a $C_6$–$C_{15}$ aryl group fused to two alkylene carbon atoms;

to citalopram, the process comprising subjecting the compound of Formula (I) to a one-pot reaction with two or more acidic dehydrating agents.

28. A process according to claim 27 wherein the acidic dehydrating agent comprises a halide or an oxyhalide compound of at least one Group V or Group VI element, or a mixture thereof.

29. A process according to claim 27 wherein the acidic dehydrating agent comprises a halide or an oxyhalide compound of phosphorus or sulfur.

30. A process according to claim 27 wherein the compound, is subjected to reaction with $PCl_3$, $PCl_5$, $POCl_3$, $SOCl_2$ or a combination thereof.

31. A process according to claim 27 wherein the compound of Formula (1) is subjected to reaction with a combination of two or more of $PCl_3$, $PCl_5$, $POCl_3$ and $SOCl_2$.

32. A process according to claim 27 wherein the compound of Formula (I) is subjected to reaction with $POCl_3$ in the presence of a base and/or a basic solvent.

33. A process according to claim 27 wherein the compound of Formula (I) is subjected the reaction in one pot using $SOCl_2$ followed by $POCl_3$.

34. A process according to claim 27 wherein the compound of Formula (I) is subjected to reaction initially with $SOCl_2$ at room temperature, and subsequently with $POCl_3$ in a temperature range of between 20 to 150° C.

35. A compound of Formula (II)

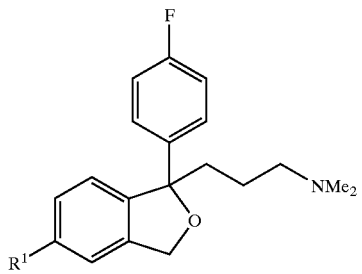

(II)

wherein $R^1$ represents a carboxylic acid group or a salt thereof.

* * * * *